US012253521B2

United States Patent
Oskeritzian et al.

(10) Patent No.: US 12,253,521 B2
(45) Date of Patent: *Mar. 18, 2025

(54) EARLY DETECTION OF COLORECTAL CANCER

(71) Applicant: UNIVERSITY OF SOUTH CAROLINA, Columbia, SC (US)

(72) Inventors: Carole A. Oskeritzian, Columbia, SC (US); Franklin Berger, Columbia, SC (US); Alena P. Chumanevich, Lexington, SC (US); John W. Fuseler, Columbia, SC (US); Nabihah I. Kumte, Columbia, SC (US); Ahmed Aladhami, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,286

(22) Filed: Jun. 29, 2023

(65) Prior Publication Data

US 2023/0341402 A1  Oct. 26, 2023

Related U.S. Application Data

(63) Continuation of application No. 16/720,309, filed on Dec. 19, 2019, now Pat. No. 11,714,088.

(Continued)

(51) Int. Cl.
*G01N 33/574* (2006.01)
*A61B 10/00* (2006.01)
(Continued)

(52) U.S. Cl.
CPC ... *G01N 33/57419* (2013.01); *A61B 10/0096* (2013.01); *A61B 10/02* (2013.01);
(Continued)

(58) Field of Classification Search
None
See application file for complete search history.

(56) References Cited

U.S. PATENT DOCUMENTS

2014/0154690 A1    6/2014  Loktionov
2017/0166955 A1*   6/2017  Birnboim ........... C12N 15/1003
(Continued)

FOREIGN PATENT DOCUMENTS

JP    2018161469 A  * 10/2018

OTHER PUBLICATIONS

Rajpoot et al., "SVM Optimization for Hyperspectral Colon Tissue Cell Classification," International Conference on Medical Image Computing and Computer-Assisted Intervention, Springer, Berlin, Heidelberg, 2004, pp. 829-837 (Year: 2004).*

(Continued)

*Primary Examiner* — Christopher Braniff
(74) *Attorney, Agent, or Firm* — DORITY & MANNING, P.A.

(57) ABSTRACT

Methods and systems for detection of precancerous colorectal cancerous lesions and early stage colorectal cancer are described. The methods and systems include examination of a rectal cell sample for the presence of mast cells in a field effect detection regime. The methods can incorporate swab-based cell collection, optionally storage and transportation of a cell sample, and/or computer-aided diagnosis.

14 Claims, 3 Drawing Sheets

Related U.S. Application Data (60) Provisional application No. 62/807,403, filed on Feb. 19, 2019.

(51) Int. Cl.
*A61B 10/02* (2006.01)
*G01N 1/30* (2006.01)
*G01N 33/50* (2006.01)

(52) U.S. Cl.
CPC .......... *G01N 1/30* (2013.01); *G01N 33/5091* (2013.01); *G01N 2001/302* (2013.01)

(56) References Cited

U.S. PATENT DOCUMENTS

2018/0168490 A1* 6/2018 Jones .................. A61B 5/7282
2020/0049599 A1* 2/2020 Alexander ............. A61P 35/00

OTHER PUBLICATIONS

ACS, "Colorectal Cancer Facts & Figures 2017-2019" *Am. Canc. Soc.* (2017) pp. 1-40.
Akin, et al. "Mast cell activation syndrome: Proposed diagnostic criteria" *J. Aller. Clin. Immun.* 126 (2010) pp. 1099-1104.
Anderson, et al. "A fractal analysis of the radial distribution of bronchial capillaries around large airways" *J. Appl. Physiol.* 98 (2005) pp. 850-855.
Aon, et al. "The scale-free dynamics of eukaryotic cells" *PLoS One* 3:e3624 (2008) pp. 1-6.
Arock, et al. "Differentiation of human basophils: An overview of recent advances and pending questions" *J. Leuko. Biol.* 71 (2002) pp. 557-564.
Backman, et al. "Light-scattering technologies for field carcinogenesis detection: a modality for endoscopic prescreening" *Gastroenterology* 140 (2011) pp. 35-41.
Bartnikas, et al. "Epicutaneous sensitization results in IgE-dependent intestinal mast cell expansion and food-induced anaphylaxis" *J. Aller. Clin. Immun.* 131 (2013) pp. 451-460.
Bossuyt, et al. "The STARD Initiative" *Lancet* 361 (2003) p. 71.
Brown, et al "The fractal nature of nature: Power laws, ecological complexity and biodiversity" *Phil. Trans. R. Soc. Lond. B* 357 (2002) pp. 619-626.
Chumanevich, et al. "Sphingosine-1-Phosphate/Sphingosine-1-Phosphate Receptor 2 Axis Can Promote Mouse and Human Primary Mast Cell Angiogenic Potential through Upregulation of Vascular Endothelial Growth Factor-A and Matrix Metalloproteinase-2" *Mediators Inflamm.* 2016:1503206 (2016) pp. 1-8.
Cinelli, et al. "Comparative analysis and physiological impact of different tissue biopsy methodologies used for the genotyping of laboratory mice" *Lab. Anim.* 41 (2007) pp. 174-184.
Corpet, et al. "Point: From animal models to prevention of colon cancer. Systematic review of chemoprevention in min mice and choice of the model system" *Canc. Epidemiol. Biomark. Pre.* 12 (2003) pp. 391-400.
Cui, et al. "Resveratrol suppresses colitis and colon cancer associated with colitis" *Canc. Prev. Res.* 3 (2010) pp. 549-559.
Da Silva, et al. "Mast cell function: A new vision of an old cell" *J. Histochem. Cytochem.* 62 (2014) pp. 698-738.
Damania, et al. "Nanocytology of rectal colonocytes to assess risk of colon cancer based on field cancerization" *Canc. Res.* 72 (2012) pp. 2720-2727.
De Robertis, et al. "The AOM/DSS murine model for the study of colon carcinogenesis: From pathways to diagnosis and therapy studies" *J. Carcinog*, 10 (2011).
Di Ieva, A. "Fractal analysis of microvascular networks I malignant brain tumors" *Clin. Neuropath.* 31 (2012) pp. 342-351.
Di Ieva, et al. "Fractal dimension as a quantitator of the microvasculature of normal and adenomatous pituitary tissue" *J. Anat.* 211 (2007) pp. 673-680.
Dioguardi, et al. "Metrically measuring liver biopsy: a chronic hepatitis B and C computer-aided morphologic description" *World J. Gastroenterol.* 14 (2008) pp. 7335-7344.
Dioguardi, et al. "Liver fibrosis and tissue architectural change measurement using fractal-rectified metrics and Hurst's exponent" *World J. Gastroenterol.* 12 (2006) pp. 2187-2194.
Doubal, et al. "Fractal analysis of retinal vessels suggests that a distinct vasculopathy causes lacunar stroke" *Neurology* 74 (2010) pp. 1102-1107.
Ferro, et al. "Fractal characteristics of May-Grünwald-Giemsa stained chromatin are independent prognostic factors for survival in multiple myeloma" *PLoS One* 6:e20706 (2011) pp. 1-8.
Fuseler, et al. "Modulation of the migration and differentiation potential of adult bone marrow stromal stem cells by nitric oxide" *Biomaterials* 33 (2012) pp. 1032-1043.
Fuseler, et al. "Fractal and image analysis of the microvasculature in normal intestinal submucosa and intestinal polyps in Apc$^{Min/+}$ mice" *Microsc. Microanal.* 16 (2010) pp. 73-79.
Fuseler, et al. "Fractal and image analysis of morphological changes in the actin cytoskeleton of neonatal cardiac fibroblasts in response to mechanical stretch" *Microsc. Microanal.* 13 (2007) pp. 133-143.
Fuseler, et al. "Analysis and quantitation of NF-κB nuclear translocation in tumor necrosis factor alpha (TNF-α) activated vascular endothelial cells" *Microsc. Microanal.* 12 (2006) pp. 269-276.
Galli, et al. "IgE and mast cells in allergic disease" *Nat. Immun.* 18 (2012) pp. 693-704.
Galli, et al. "Phenotypic and functional plasticity of cells of innate immunity: Macrophages, mast cells and neutrophils" *Nat. Immun.* 12 (2011) pp. 1035-1044.
Galli, et al. "Immunomodulatory mast cells: Negative, as well as positive, regulators of immunity" *Nat. Rev. Immun.* 8 (2008) pp. 478-486.
Gerber, et al. "The top skin-associated genes: A comparative analysis of human and mouse skin transcriptomes" *Biol. Chem.* 395 (2014) pp. 577-591.
Giannou, et al. "Mast cells mediate malignant pleural effusion formation" *J. Clin. Invest.* 125 (2015) pp. 2317-2334.
Gladstein, et al. "Correlating colorectal cancer risk with field carcinogenesis progression using partial wave spectroscopic microscopy" *Canc. Med.* 7 (2018) pp. 2109-2120.
Grizzi, et al. "Quantitative evaluation and modelling of two-dimensional neovascular network complexity: The surface fractal dimension" *BMC Cancer* 5 (2005) pp. 14-23.
Grizzi, et al. "A fractal scoring system for quantifying active collagen synthesis during chronic liver disease" *Int'l. J. Chaos Theo. Appl.* 21 (1999) pp. 262-266.
Hamilton, et al. "Mast cell activation syndrome: A newly recognized disorder with systemic clinical manifestations" *J. Aller. Clin. Immun.* 128 (2011) pp. 147-152.
Hart, et al. "Age-related changes in dermal mast cell prevalence in BALB/c mice: Functional importance and correlation with dermal mast cell expression of Kit" *Immunology* 98 (1999) pp. 352-356.
Hart, et al. "Dermal mast cells determine susceptibility to ultraviolet B-induced systemic suppression of contact hypersensitivity responses in mice" *J. Exp. Med.* 187 (1998) pp. 2045-2053.
Hochberg, et al. "More powerful procedures for multiple significance testing" *Stat. Med.* 9 (1990) pp. 811-818. (Abstract only).
Holm, S. "A simple sequentially rejective multiple test procedure" *Scand. J. Statist.* 6 (1979) pp. 65-70.
Imperiale, et al. "Multitarget stool DNA testing for colorectal-cancer screening" *N. Engl. J. Med.* 370 (2014) pp. 1287-1297.
Irani, et al. "Two types of human mast cells that have distinct neutral protease compositions" *PNAS* 83 (1986) pp. 4464-4468.
Jelinek, et al. "The morphology and classification of a ganglion cells in the rat retinae: A fractal analysis study" *J. Neurosci. Meth.* 201 (2011) pp. 281-287.
Johnson-Henry, et al. "Probiotics reduce bacterial colonization and gastric inflammation in *H. pylori*-infected mice" *Dig. Dis. Sci.* 49 (2004) pp. 1095-1102.
Kalesnikoff, et al. "New developments in mast cell biology" *Nat. Immunol.* 9 (2008) pp. 1215-1223.

(56) References Cited

OTHER PUBLICATIONS

Kekelidze, et al. "Colorectal cancer: current imaging methods and future perspectives for the diagnosis, staging and therapeutic response evaluation" *World J. Gastroenterol.* 19 (2013) pp. 8502-8514.
Kucherlapati, et al. "An Msh2 conditional knockout mouse for studying intestinal cancer and testing anticancer agents" *Gastroenterology* 138 (2010) pp. 993-1002.
Lagunoff, D. "Analysis of dye binding sites in mast cell granules" *Biochemistry* 19 (1974) pp. 3982-3986.
Lahm, et al. "Identification of transgenic mice by direct PCR analysis of lysates of epithelial cells obtained from the inner surface of the rectum" *Transgen. Res.* 7 (1998) pp. 131-134.
Mandelbrot, B.B. "The Fractal Geometry of Nature" *W.H. Freeman and Company* (1982) pp. 1-468.
Manera, et al. "The use of fractal dimension and lacunarity in the characterization of mast cell degranulation in rainbow trout (Onchorhynchus mykiss)" *J. Microsc.* 256 (2014) pp. 82-89.
Marichal, et al. "Mast cells: potential positive and negative roles in tumor biology" *Canc. Immunol. Res.* 1 (2013) pp. 269-279.
Marshall, J.S. "Mast-cell responses to pathogens" *Nat. Rev. Immunol.* 4 (2004) pp. 787-799.
McAlearney, et al. "Racial differences in colorectal cancer screening practices and knowledge within a low-income population" *Cancer* 112 (2008) pp. 391-398.
McIntyre, et al. "Mouse models of colorectal cancer as preclinical models" *Bioassays* 37 (2015) pp. 909-920.
McNally, et al. "Fractal geometry in the nucleus" *EMBO J.* 29 (2010) pp. 2-3.
Metz, C.E. "Basic principles of ROC analysis" *Semin. Nucl. Med.* 8 (1978) pp. 283-298.
Moledina, et al. "Fractal branching quantifies vascular changes and predicts survival in pulmonary hypertension: a proof of principle study" *Heart* 97 (2011) pp. 1245-1249.
Moon, et al. "Mast cell mediators: Their differential release and the secretory pathways involved" *Front. Immunol.* 5 (2014) pp. 1-18.
Moser, et al. "A dominant mutation that predisposes to multiple intestinal neoplasia in the mouse" *Science* 247 (1990) pp. 322-324.
Nezadal, et al. "The boxcounting: Critical study" *4th Conf. Pred. Synerg. More* (2001) p. 18.
Oldford, et al. "Mast cells as targets for immunotherapy of solid tumors" *Mol. Immunol.* 63 (2015) pp. 113-124.
Oskeritzian, et al. "The sphingosine-1-phosphate/sphingosine-1-phosphate receptor 2 axis regulates early airway T-cell infiltration in murine mast cell-dependent acute allergic responses" *J. Aller. Clin. Immunol.* 135(4) (2015) pp. 1008-1018.
Oskeritzian, C.A. "Mast cell plasticity and sphingosine-1-phosphate in immunity, inflammation and cancer" *Mol. Immunol.* 63 (2015) pp. 104-112.
Oskeritzian, et al. "Essential roles of sphingosine-1-phosphate receptor 2 in human mast cell activation, anaphylaxis, and pulmonary edema" *J. Exp. Med.* 207(3) (2010) pp. 465-474.
Oskeritzian, et al. "Distinct roles of sphingosine kinases 1 and 2 in human mast cell functions" *Blood* 111 (2008) pp. 4193-4200.
Parang, et al. "AOM/DSS model of colitis-associated cancer" *Meth. Mol. Biol.* 1422 (2016) pp. 297-307.
Patel, et al. "Colorectal cancer in the young" *Curr. Gastroenter. Rep.* 20:15 (2018) pp. 1-12.
Poutahidis, et al. "CD4+ lymphocytes modulate prostate cancer progression in mice" Int 'l. J. Canc. 125 (2009) pp. 868-878.
Qian, et al. "Fractal dimension as a measure of altered actin cytoskeleton in MC3T3-E1 cells under simulated microgravity using 3-D/2-D clinostats" *IEEE Trans. Biomed. Eng.* 59 (2012) pp. 1374-1380.
Rafail, et al. "Complement deficiency promotes cutaneous wound healing in mice" *J. Immunol.* 194 (2015) pp. 1285-1291.
Reber, et al. "New models for analyzing mast cell functions in vivo" *Trends Immunol.* 33 (2012) pp. 613-625.
Rho, et al. "Protein and glycomic plasma markers for early detection of adenoma and colon cancer" *Gut* 67 (2018) pp. 473-484.
Ribatti, D. "Mast cells and macrophages exert beneficial and detrimental effects on tumor progression and angiogenesis" *Immunol. Lett.* 152 (2013) pp. 83-88.
Rogers, et al. "Regulation of NF-κB activation and nuclear translocation by exogenous nitric oxide (NO) donors in TNF-α activated vascular endothelial cells" *Nitric Oxide* 16 (2007) pp. 379-391.
Schneikert, et al. "The canonical Wnt signaling pathway and its APC partner in colon cancer development" *Gut* 56 (2007) pp. 417-425.
Schwartz, et al. "Tryptase levels as an indicator of mast-cell activation in systemic anaphylaxis and mastocytosis" *N. Engl. J. Med.* 316 (1987) pp. 1622-1626.
Sedivy, et al. "Short-term rhythmic proliferation of human breast cancer cell lines: Surface effects and fractal growth patterns" *J. Pathol.* 197 (2002) pp. 163-169.
Slaughter, et al. "Field cancerization in oral stratified squamous epithelium; clinical implications of multicentric origin" *Cancer* 6 (1953) pp. 963-968.
Smith, et al. "Fractal methods and results in cellular morphology-dimensions, lacunarity and multifractals" *J. Neurosci. Meth.* 39 (1996) pp. 123-136.
Streba, et al. "A pilot study on the role of fractal analysis in the microscopic evaluation of colorectal cancers" *Rom. J. Morph. Embryol.* 56 (2015) pp. 191-196.
Subramanian, et al. "Nanoscale cellular changes in field carcinogenesis detected by partial wave spectroscopy" *Canc. Res.* 69 (2009) pp. 5357-5363.
Subramanian, et al. "Optical methodology for detecting histologically unapparent nanoscale consequences of genetic alterations in biological cells" *PNAS* 105 (2008) pp. 20118-20123.
Suzuki, et al. "Strain differences in the susceptibility to azoxymethane and dextran sodium sulfate-induced colon carcinogenesis in mice" *Carcinogenesis* 27 (2006) pp. 162-169.
Taketo, M.M. "Wnt signaling and gastrointestinal tumorigenesis in mouse models" *Oncogene* 25 (2006) pp. 7522-7530.
Thamrin, et al. "Fractals for physicians" *Paediat. Resp. Rev.* 11 (2010) pp. 123-131.
Theoharides, et al. "Mast cells and inflammation" *Biochim. Biophys. Acta* 1822 (2012) pp. 21-33.
Valent, et al. "Clinical and laboratory parameters of mast cell activation as basis for the formulation of diagnostic criteria" Int'l. *Arch. Aller. Immun.* 156 (2011) pp. 119-127.
Varricchi, et al. "Are mast cells MASTers in cancer?" *Front. Immun.* 8:424 (2017) pp. 1-13.
Voehringer, D. (2013). Protective and pathological roles of mast cells and basophils. *Nat Rev Immunol* 13, 362-375.
Wallace, et al. "Race and prevalence of large bowel polyps among the low-income and uninsured in South Carolina" *Dig. Dis. Sci.* 61 (2016) pp. 265-272.
Walter, et al. "Digital image processing and analysis" *Video Microscopy* (1986) pp. 327-392. (Abstract Preview Only).
Wedman, et al. "Mast cells and sphingosine-1-phosphate underlie prelesional remodeling in a mouse model of eczema" *Allergy* 73(2) (2018) pp. 405-415.
Wedman, et al. "A New Image Analysis Method Based on Morphometric and Fractal Parameters for Rapid Evaluation of In Situ Mammalian Mast Cell Status" *Microsc. Microanal.* 21(6) (2015) pp. 1573-1581.
Welch, et al. "Colorectal cancer on the decline-Why screening can't explain it all" *N. Engl. J. Med.* 374 (2016) pp. 1605-1607.
Wernersson, et al. "Mast cell secretory granules: Armed for battle" *Nat. Rev. Immunol.* 14 (2014) pp. 478-494.
Wick, et al. "Quantitative measurement of cell migration using time lapse video microscopy and non-linear system analysis" *Histochem. Cell Bio.* 119 (2003) pp. 15-20.
Widman et al., "A new Image Analysis Method on Morphometric and Fractal Parameters for Rapid Evaluation of In Situ Mammalian Mast Cell Status," *Microscopy and Microanalysis*, Oct. 2015, pp. 1-9. (Year: 2015).
Wolf, et al. "Colorectal cancer screening for average-risk adults: 2018 guideline update from the American Cancer Society" *CA Canc. J. Clin.* 68 (2018) pp. 250-281.

(56) References Cited

OTHER PUBLICATIONS

Wolters, et al. "Tissue-selective mast cell reconstitution and differential lung gene expression in mast cell-deficient KitW-sh/KitWash sash mice" *Clin. Exp. Aller.* 35 (2005) pp. 82-88.

Zhang, et al. "A three-dimensional fractal analysis method for quantifying white matter structure in human brain" *J. Neurosci. Meth.* 150 (2006) pp. 242-253.

Zouien, et al. "Applying fractal dimension and image analysis to quantify fibrotic collagen deposition and organization in the normal and hypertensive heart" *Microsc. Microanal.* 20 (2014) pp. 1134-1144.

Zweig, et al. "Receiver-operating characteristic (ROC) plots: a fundamental evaluation tool in clinical medicine" *Clin. Chem.* 39 (1993) pp. 561-577.

* cited by examiner

EARLY DETECTION OF COLORECTAL CANCER

CROSS REFERENCE TO RELATED APPLICATION

This application is a continuation application of U.S. patent application Ser. No. 16/720,309, having a filing date of Dec. 19, 2019, which claims filing benefit of U.S. Provisional Patent Application Ser. No. 62/807,403, having a filing date of Feb. 19, 2019, entitled "System and Method for Detecting Colorectal Cancer," both of which are incorporated herein by reference for all purposes.

FEDERAL RESEARCH STATEMENT

This invention was made with Government support under Grant No. P30 GM103336, awarded by the National Institutes of Health. The Government has certain rights in the invention.

BACKGROUND

Screening for colorectal cancer (CRC) can successfully detect polyps and prevent polyp-to-cancer progression. Early detection substantially improves morbidity and mortality. Unfortunately, current screening methods suffer low adherence rates. Current methods include a yearly fecal immunochemical test (FIT) that has low sensitivity for adenoma detection and invasive endoscopy (colonoscopy, flexible sigmoidoscopy). The FDA-approved Cologuard® screening system combines FIT with DNA analysis for improved sensitivity but remains under-prescribed due to high cost and burdensome sample collection. Structural imaging, including partial wave spectroscopic microscopy and diffusion-weighted imaging, shows promise for improved screening outcomes, but current methods have limitations associated with sophisticated data interpretation and high-cost equipment, necessitating highly trained observers.

Guidelines published in 2018 by the American Cancer Society were modified to recommend CRC screening to start at age 45, lowered from 50 before the update. This recommendation reflects earlier onset of CRC that increasingly occurs in patients aged 20 to 40 who are diagnosed when already symptomatic. Unfortunately, younger patients are one of the demographics showing high reluctance for CRC screening.

Ongoing concerns in CRC research encompass the unmet need for improved, affordable, and less invasive diagnostic/prognostic tools. Only a minority of symptomatic patients is detected with early stage disease, so the development of new screening strategies for the prevention and early detection of CRC is vitally important to improve survival from CRC.

What is needed in the art is a screening method and system that offers low cost, accessible, and less invasive screening modalities.

SUMMARY

According to one embodiment, disclosed is a method for early detection of CRC. A method can include collecting a cell sample from a rectal area of a subject, staining the cell sample with a stain that can be used to identify mast cells (e.g., chloroacetate esterase (CAE) or methylene blue (MB)) and examining the stained cell sample to determine the presence of mast cells in the sample, the presence of mast cells in the cell sample being an indication of precancerous polyps or CRC in the colon of the subject.

Also disclosed is a system that can be utilized in early detection of CRC. A system can include a rectal swab, a buffer configured to retain cells collected by the swab, a container that is configured to carry the buffer and the cells retained therein (for instance during storage, transportation, etc.), and a cap that is configured to seal the container.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

Disclosed is a swab-associated method and system for detection of precancerous CRC lesions and early stage CRC. The methods and systems can provide a detection approach that is simple and affordable. In one embodiment, the methods can incorporate computer-aided diagnosis, which can serve to improve and validate diagnosis of early stage CRC or precancerous polyps in the colon.

The CRC detection approach can significantly promote CRC screening over conventional approaches, at least due to low cost, ease of procedure (e.g., a sample collection that can be carried out in a few seconds), and potential for rapid sample processing (e.g., less than one hour). In one embodiment, a method can utilize a computer-based analysis technique that does not require expensive components or highly trained personnel. Moreover, testing systems can be portable and, as such, can be utilized in home settings, as well as clinics, and do not require travel or treatment by the patient at a hospital or large, urban testing facility.

Disclosed methods and systems are based upon field effect detection of mast cells (MC) among rectal cells. MC are innate immune cells that function as initiators and regulators of many processes, including cancer. Long-lived tissue-resident sentinel cells, MC are located close to the intestinal epithelium and blood vessels at homeostasis. MC accumulation is an essential feature of intestinal polyposis in mice and of invasive intestinal lesions. Moreover, colonic mast cells (MC) are predominantly located in the distal colon, which is noteworthy as approximately ⅔ of human CRC are located in the rectum or the sigmoid colon, and early-onset CRC in young patients are also disproportionately located in the distal colon.

The detection of MC among rectal cells as described can constitute a field effect-related correlation of pre-neoplastic lesions present upstream in the colon. Field effect (or field carcinogenesis) is based on the occurrence of subtle alterations prior to and at a distance from cancer foci. Methods have been developed to detect field-effect changes in other detection regimes, ranging from detection of plasma markers to detection of nanoscopic nuclear transformations. Unfortunately, these methods require costly equipment and personnel training for data interpretation, preventing advance to clinical practice.

The early CRC detection approach is based upon the understanding that the cellular composition of cells sloughed from premalignant colons will differ from those shed from healthy colons. More specifically, the early CRC detection method is based on a simple "binary" determination, i.e., MC in a rectal cell sample indicates the presence of precancerous polyps in the colon and no MC in a rectal cell sample indicates no precancerous polyps in the colon.

Figure 1:
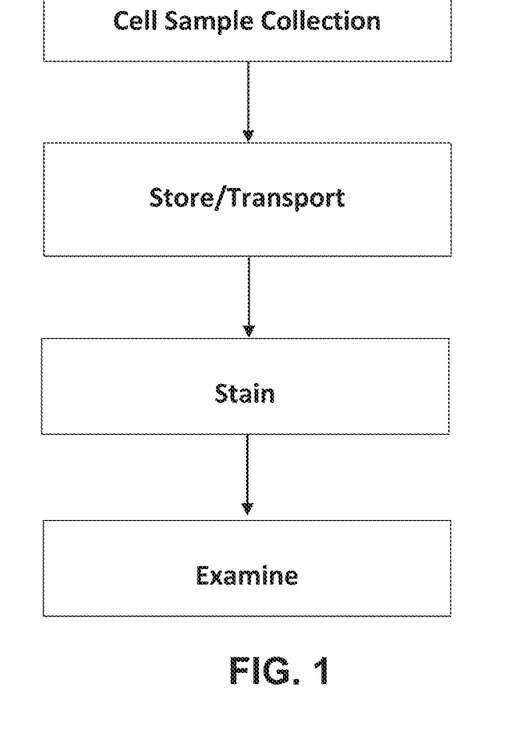
FIG. 1 presents a flow diagram for a method as disclosed herein.

FIG. 1 illustrates a flow chart for one embodiment of an early CRC detection method. As indicated, a method can include collection of a rectal cell sample. While any cell sample collection approach can be utilized, in one embodiment, a rectal cell sample can be collected by use of a swab, which can be used to quickly and gently collect a cell sample by a health care provider or by a subject in a self-collection regime.

Figure 2:
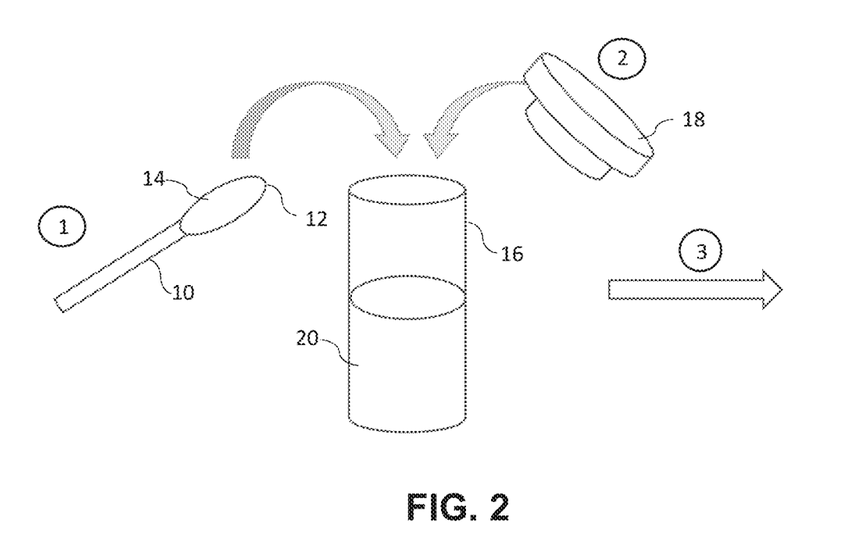
FIG. 2 schematically illustrates a system as disclosed herein.

In one particular embodiment, a cell sample collection can be carried out with a flocked swab 10, as illustrated in FIG. 2. Designed for improved cell collection and rapid elution, flocked swabs are similar to cotton/fiber swabs except that the tip 12 of the applicator 14 is coated with nylon microfibers that can act as a soft brush. Flocked swabs as may be utilized are generally known in the art and available on the open marked, e.g., Puritan® HydraFlock® flocked swabs, PurFlock Ultra® flocked swabs, etc. During a procedure, cells in the rectal area, including any colon-shed MC, can be collected on the applicator 14 by gentle rectal swabbing. Beneficially, a procedure to collect a cell sample does not require anesthesia, is minimally invasive, and only takes a few seconds (e.g., about 5 seconds).

In one embodiment, the cells of the swab can be stained and examined for the presence of MC immediately following collection. In another embodiment, the collected cells can be stored or transported following collection of a cell sample from a rectal area. In such an embodiment, cells from the swab, the entire cell-loaded swab, or the applicator end of the cell-loaded swab can be stored and/or transported prior to examination of the sample for the presence of MC. For instance, and as indicated in FIG. 2, the applicator 14 can be placed in a container 16 as indicated at 1 on FIG. 2. The container 16 can also carry a suitable solution 20, e.g., a buffer solution such as an isotonic phosphate-buffered saline (PBS) solution, to safely store and retain the cells carried on the applicator 14. Cells of the collected sample can spontaneously release from the applicator 14 into the solution 20. However, to encourage more complete release of the cells, the applicator 10 can be stirred in the solution 20, e.g., by gentle vortexing to release the cell sample.

The container 16 can be fitted with a cap 18 as indicated at 2 on FIG. 2. The cap 18 can seal the container 16 and protect the sample during storage (e.g., cold storage), transportation, etc., as indicated at 3 until further processing.

In some embodiments, prior to staining cells of the cell sample for detection of any mast cells, the cell sample can be further processed. For instance, the cells of the sample can be concentrated, fixed, washed, etc. prior to staining. In one embodiment, cells retained in the solution 20 can be collected via centrifugation. After centrifugation, supernatants can be eliminated and cell pellets resuspended in a fixative, e.g., a 4% paraformaldehyde solution. It should be understood, however, that any pre-processing methods as are generally known in the art are encompassed herein, and methods other than fixing and staining swab-collected cells in suspension may also be utilized. For instance, cytospins or swab cell deposition in small drops on microscopy slides can be carried out followed by quick airdrying.

Following any pre-processing, the cells of the sample can be washed prior to staining; for instance, the cells can be washed by centrifugation to eliminate any fixative or other pre-processing material.

The cell sample can be stained using a detectable material that can identify the presence of MC in the sample. For instance, the MC can be identified as such by use of chloroacetate esterase (CAE, available from Millipore Sigma) or methylene blue (MB, available from Millipore Sigma) staining. Staining of the cells can be carried out according to standard practice and following the manufacturer's instructions. Following staining of the cell sample, the sample can be examined for the presence of MC by study of the resulting stained cell sample.

Certain stains can stain cells types in addition to MC. For instance, CAE can stain neutrophils, as well as other members of the polymorphonuclear (PMN) cells family, in addition to MC. To clearly distinguish between MC and other stained cells of a sample, comparative study can be carried out during the examination process. For instance, to distinguish between CAE-stained MC and CAE-stained PMN cells, nuclear morphology studies can be performed. MC are mononuclear cells with a well-defined round single nucleus, whereas PMN are polymorphonuclear cells featuring a polylobed nucleus of typically 3 lobes or more. Thus, relatively simple examination of the stained cell sample can differentiate MC from other stained cells in such an embodiment.

In one embodiment, a cell sample can be stained with multiple, different materials so as to clearly differentiate the presence of MC from other cell types in the sample. For instance, in one embodiment, following staining with CAE, hematoxylin counterstaining can be performed. This further step can be used to distinguish MC from PMN, as hematoxylin can stain nuclei in blue, and visual study of the results can provide a clear differentiating indicia of the two cell types (mononuclear and polymorphonuclear).

In one embodiment, methylene blue (MB) staining can be used to detect MC in a sample. MB stains the nuclei of all cells in blue, but MC cytoplasm will be stained purple due to metachromatic staining of the proteoglycans, which are the main components of MC cytoplasmic granules.

Following staining, the sample can be examined to determine the presence or quantity of MC cells in the sample. For instance, the stained sample can be washed and transferred to microscopy slides for analysis.

In one embodiment, a computerized imaging approach can be used to detect MC among cells of the cell sample. Computerized imaging approaches as may be utilized have been described previously, for instance by Wedman et al., Microsc Microanal. 2015; 21(6):1573-81 and Wedman et al. Front Immunol, 2017; 8:424.

A computerized approach can be used for identification of the presence of MC in a sample, as well as for quantification of the cells in a sample. In one embodiment, a computerized method can identify MC in a sample through the definition of numerical boundary values for multi-morphometric descriptors. In a typical computerized imaging approach, morphometrics, such as area of an MC cell, and integrated optical density of an MC cell can be utilized to differentiate MC cells from other cells in a digitized sample. Details of one embodiment of such an approach are described further in the example section herein.

Beneficially, imaging systems as may be utilized in a computerized imaging approach are relatively inexpensive and, as such, are accessible to private practice, as well as clinical settings. Moreover, sample preparation and computed analysis of such techniques can be straightforward and do not require any special equipment or any special training. Furthermore, the results can be available quickly; for instance, the same day as sample collection in those embodiments in which a sample is collected at or near the analysis location. As such, computerized analysis can optimize the clinical workflow, as well as provide standardized and automated measurements, leading to early diagnosis and prevention of CRC through identification of rectal area cell composition change as a premalignant polyp diagnostic tool.

Of course, the examination and detection methodology is not limited to a computerized approach. In some embodiments, other identification methods can be utilized, optionally in conjunction with a computerized identification approach. For instance, in one embodiment, following identification of MC in a sample via a computerized identification approach, a follow-up detection approach can be utilized to confirm the initial finding.

By way of example, and without limitation, MC can be identified by an immunohistochemistry (IHC) approach using an antibody (Ab) directed against MC-restricted tryptase. This method utilizes parallel staining with an isotype-matched negative control Ab and, as such, would require splitting the sample of swab suspension into two parts. This may present issues as it could decrease the sensitivity of the assay, but it still presents a viable detection approach.

The disclosed MC-based screening method for CRC has the potential to significantly transform clinical practice as it holds promise as a noninvasive, rapid, objective, and cost-effective method to analyze swab-collected cells. Adaptable to primary care setting, specimen collection, processing, and analysis do not require expensive equipment, trained personnel, or complex data interpretation. This approach can change the current paradigm of CRC screening and improve CRC prevention through increased uptake of screening and detection of early-stage disease.

The present disclosure may be better understood with reference to the Examples set forth below.

Example

Mice heterozygous for the Apc gene (ApcMin/+) (Min mice) were studied at 5 weeks and 7-8 weeks of age to confirm that the Min mice display some intestinal polyps and are CRCprone by 7-8 weeks of age. Azoxymethane (AOM) was used to induce CRC in the mice. When combined with several rounds of the inflammatory agent dextran sulfate sodium (DSS) in drinking water, AOM will cause colonic tumors within 10 weeks. Inflammation starts during the first week of DSS administration, leading first to colitis without cancer, which allowed study of whether or not inflammation per se may induce MC shedding. Thus, the AOM/DSS model provided insights into inflammation-driven CRC, beginning with colitis, as seen in ulcerative colitis or Crohn's disease of humans. This chemically-induced model of CRC was used at it is applicable to various mouse strains, addressing genetic variability, and also as it recapitulates human CRC where tumors are more frequent in the distal part of the colon.

Rectal swabbing of the mice was performed using a tail-first restrainer and flocked swabs with handles. After swabbing, swab tips were transferred into a 15-ml conical tube containing 300 µl of isotonic PBS buffer. Tubes were capped and kept on ice until processing. Collected material was released into the buffer by gentle vortexing and removing the swabs. After centrifugation, supernatants were eliminated and pellets resuspended in fresh 1% paraformaldehyde to fix the cells for 15 minutes at room temperature (RT). Tubes were centrifuged to collect pellets that were next stained in suspension with chloroacetate esterase (CAE) to detect MC, following the manufacturer's instructions (Millipore Sigma), and hematoxylin counterstaining for nuclear morphology in some samples as indicated herein. In parallel, colons of euthanized mice were collected and rolled from the distal to proximal end in a "Swiss roll" format, fixed, and processed for CAE staining.

Figure 3:
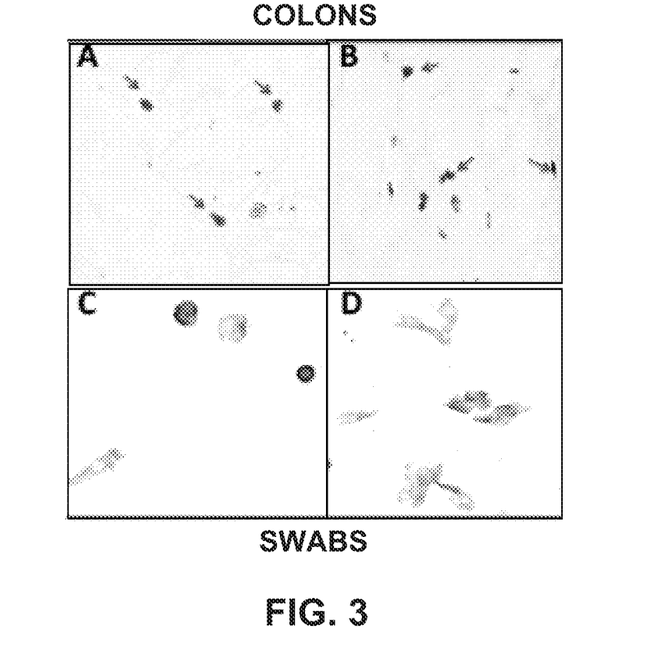
FIG. 3 presents representative images of mast cell detection results of colon (A, B) and rectal swab (C, D) samples of 5-week-old male mice heterozygous for the Apc gene (ApcMin/+) (Min) (B, D) and wild type (WT) (A, C).

FIG. 3 presents representative imaging results of colon (A, B) and rectal swab (C, D) samples for 5-week-old Min (B, D) and WT (A, C) mice. As indicated by the arrows, colonic MC were detectable by CAE staining. No difference between genotypes was noticed in the number or distribution of MC, with the majority of MC located at the distal end of the colons. Also, no polyps were observed and no MC were detectable in the CAE-negative swab specimens for either genotype at 5 weeks of age (C, D). No hematoxylin counterstain was performed in the images of FIG. 3. Images were taken with a DM2500 microscope system equipped with a DFC365FX digital camera Leica Microsystems, Inc.), collected as TIFF files at low 20× (A, B) and high 40× (C, D) magnifications.

Figure 4:
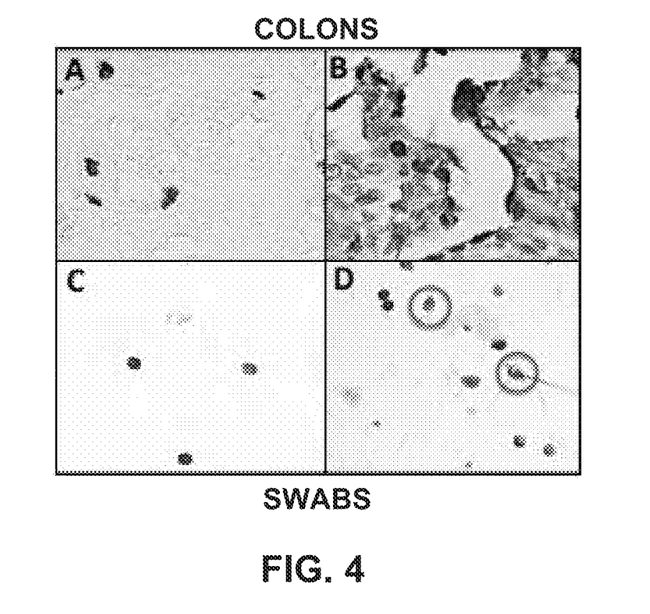
FIG. 4 presents representative images of mast cell detection results of colon (A, B) and rectal swab (C, D) samples of 7-8-week-old Min (B, D) and WT (A, C) mice.

FIG. 4 presents representative imaging results of colon (A, B) and rectal swab (C, D) samples for 7-8-week-old Min (B, D) and WT (A, C) mice. Hematoxylin counterstain was performed on the sample imaged in B to emphasize disruption in colons of Min mice. As indicated, while colonic MC remained randomly distributed in WT mice (A), they clustered in the polypoid lesions of Min mice (B). No polyps were present in the colons of WT mice (A), and no MC were detectable in the swab specimens of WT mice (no circled cells in FIG. 4C). CAE staining provided preliminary evidence that MC could be detected (2 circled cells in FIG. 4D) in the swabs of Min mice that harbored colonic precancerous polyps upstream but not in age-matched normal WT or healthy Min mice.

Figure 5:
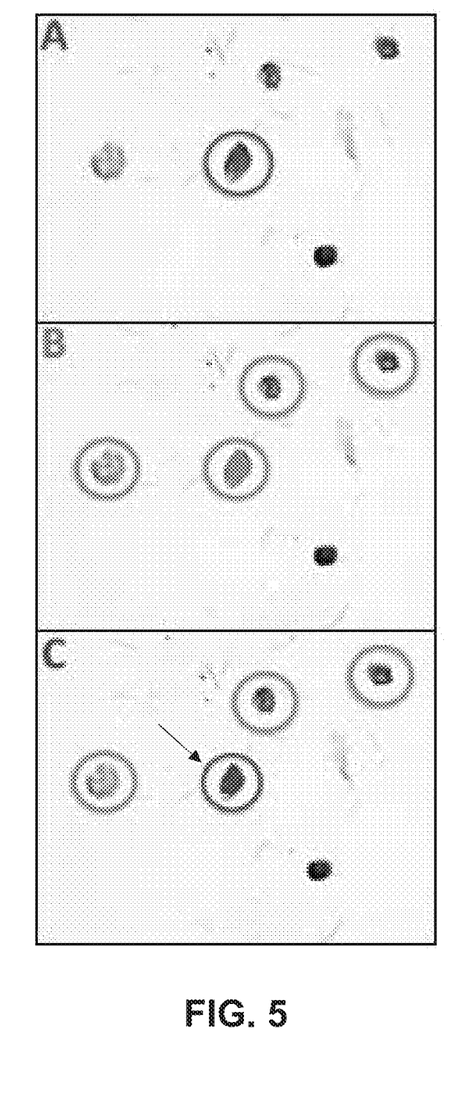
FIG. 5 presents surveying results of rectal swab images in identifying MC. At A is shown a representative image of CAE staining of swab specimens collected from a 7-8-week-old male Min mouse. At B is provided a computer-conducted survey of the same image. At C is shown the same image after applying MC-restricted morphometric descriptors.

To analyze the samples, digitized 40× images were used to define swab MC morphometrics using an image analysis software (MetaMorph® 6.1, Molecular Devices). The morphometric descriptors of area (A, $\mu m^2$), and integrated optical density (IOD, sum of the optical densities of the pixels that make up the "object", i.e., the MC) were used to generate relative density (IOD/A ratio). The descriptors were measured for threshold and isolated MC in the swabs. CAE-positive MC were defined as such at high 100× magnification by two blinded observers. One example of such defined MC is illustrated in FIG. 5 at A. Defined areas were then isolated in digitized images as individual Regions of Interest (ROI) using the Hue, Saturation, Intensity (HSI) color model of the set color threshold subroutine of Meta-Morph, as previously described (see, e.g., Wedman P, et al. Microsc Microanal. 2015; 21(6):1573-81). The area (A) of the cell measured excluded holes (non-stained regions) within the ROI. The HSI color space model is based on the principal that any color can be specified as a single point within the subspace it defines. Thus, each color may be described by three components: the Hue, a transformed gray scale value ranging from 0 to 255, that describes the color selected (red in this case); the Saturation, also ranging from 0 to 255, that signals how much the color is "polluted" with white color (low saturation refers to a pale color, whereas high saturation refers to pure, vivid color); and the Intensity value of the color, also ranging from 0 to 255, that defines how bright or dark the selected color is. The HSI values were adjusted to isolate the cytoplasmic red color characteristic of MC as a threshold region. The cytoplasmic red color was thus used to distinguish MC from other cells. From the threshold region, the area (A) of a cell and its IOD were measured using the integrated morphometry subroutine of MetaMorph®. When using threshold boundaries in an image, the IOD is defined as the weighted sum of the image histogram in which each term in the histogram is multiplied by the gray value it represents and is expressed by the following equation:

$$IOD(T1,T2) = \Sigma_{GV=T1}^{T2} H(GV) \times GV$$

in which T1 and T2 represent the upper and lower thresholds defining the ROI in the histogram, GV the gray value of each pixel, and H(GV) the gray level histogram.

Values of IOD were calculated directly from the integrated morphometry subroutine of MetaMorph®. Using the software's optical calipers, the measurements were refined by setting specific boundary conditions for area and IOD for acceptance of the signal from individual MC and to eliminate the contributions of any non-specific and background staining. This concept of IOD representing the total amount of stained material in an ROI of an image is well established. Using this model, swab MC were accurately defined by applying the following ranges as $214<H<255$; $15<S<208$; and $61<I<150$. These descriptors enabled the software to automatically threshold (i.e., discriminate signal from noise) potential MC (circled in FIG. 5 at B). Finally, when keying in MC-restricted morphometric descriptors of Area ($63.04$ $\mu m^2 < A < 513.47 \mu m^2$); Integrated Optical Density (a measure of mass, $315.98 < IOD < 918.53$); Elliptical Form Function (length ($\mu m$)—to breadth ($\mu m$) ratio of the "object", $0.987 < EFF < 4.00$); and Texture Difference Moment (roughness, higher values when large variations in color level, $1.159 < TDM < 4.081$), as described previously, the software counted actual MC (circle with arrow in FIG. 5 at C), distinguishing MC among other non MC (other circles in FIG. 5 at C).

Using this computed image surveying method, no MC could be detected in swabs collected from 7-8-week-old WT mice or from 1) 5-week-old Min or WT mice or 2) AOM/DSS- or vehicle-treated mice that do not display any precancerous polyps upstream. Of note, swab cells collected from AOM/DSS-treated mice did harbor MC, detected by the above described computerized method (data not shown).

In the AOD/DSS model using C57BL/6 (B6, the mouse strain of Min mice), no MC were detectable in the weekly collected swabs until AOM/DSS-treated (but not vehicle treated) mice developed polyps or cancer at week 10 and beyond. In this model, swabs were collected weekly after the first DSS administration until 14 weeks, where half of the animals displayed tumors at the end of the trial. Strikingly, only polyp- and/or tumor-carrying mice yielded swabs with MC demonstrating that inflammation alone did not cause MC to shed into the colonic lumen. These data strongly suggest that colonic transformation, but not inflammation, led to the presence of MC among swab-collected cells.

The appearance of MC among cells collected by rectal swabbing strongly correlated with precancerous colonic polyps in agreement with the concept of field effect.

Results were obtained using male (M) mice, as CRC incidence rates are approximately 30% higher in men than in women, while mortality rates are about 40% higher.

While certain embodiments of the disclosed subject matter have been described using specific terms, such description is for illustrative purposes only, and it is to be understood that changes and variations may be made without departing from the spirit or scope of the subject matter.

What is claimed is:

1. A method for detection of colorectal cancer or precancerous colon polyps, the method comprising:
    swabbing a rectal area of a subject and thereby collecting a cell sample on the swab;
    sealing the cell sample in a container, the container carrying a buffer solution; and
    detecting according to a computerized imaging approach the presence or quantity of sloughed colonic mast cells in the sample, wherein the computerized imaging approach comprises identifying areas of the stained cell sample that include slain-positive cells, and isolating individual regions of interest in the identified areas according to a Hue, Saturation, Intensity (HSI) color model;
    wherein the presence of the sloughed colonic mast cells in the cell sample indicates the presence of colorectal cancer or precancerous polyps in the colon of the subject.

2. The method of claim 1, wherein the swab is a flocked swab.

3. The method of claim 1, wherein all or a portion of the swab is sealed in the container with the cell sample.

4. The method of claim 1, wherein the step of detecting the presence or quantity of sloughed colonic mast cells in the sample comprises staining the cell sample.

5. The method of claim 4, further comprising concentrating, fixing, or washing the cell sample prior to staining the cell sample.

6. The method of claim 4, wherein the stain utilized in staining the cell sample comprises methylene blue or chloroacetate esterase.

7. The method of claim 6, wherein the stain comprises chloroacetate esterase, the method further comprising counterstaining the cell sample with hematoxylin.

8. The method of claim 1, wherein the computerized imaging approach further comprises the definition of boundary conditions for a morphometric descriptor.

9. The method of claim 8, wherein the morphometric descriptor includes area or integrated optical density.

10. The method of claim 1, wherein the isolated individual regions of interest comprise a Hue value between 214 and 255, a Saturation value between 15 and 208, and an Intensity value between 61 and 150.

11. The method of claim 1, wherein the step of detecting the presence or quantity of sloughed colonic mast cells in the sample comprises contacting the cell sample with an antibody directed against mast cell restricted tryptase.

12. The method of claim 1, further comprising storing or transporting the sealed container carrying the cell sample prior to detecting the presence or quantity of sloughed colonic mast cells in the sample.

13. A method for detection of colorectal cancer or precancerous colon polyps, the method comprising:
   swabbing a rectal area of a subject and thereby collecting a cell sample on the swab;
   sealing the cell sample in a container, the container carrying a buffer solution; and
   detecting according to a computerized imaging approach the presence or quantity of sloughed colonic mast cells in the sample, wherein the computerized imaging approach comprises identifying areas of the stained cell sample that include stain-positive cells, and isolating individual regions of interest in the identified areas according to a Hue, Saturation, Intensity (HSI) color model, wherein the isolated individual regions of interest comprise a Hue value between 214 and 255, a Saturation value between 15 and 208, and an Intensity value between 61 and 150;
   wherein the presence of the sloughed colonic mast cells in the cell sample indicates the presence of colorectal cancer or precancerous polyps in the colon of the subject.

14. A method for detection of colorectal cancer or precancerous colon polyps, the method comprising:
   swabbing a rectal area of a subject and thereby collecting a cell sample on the swab;
   sealing the cell sample in a container, the container carrying a buffer solution; and
   detecting according to a computerized imaging approach the presence or quantity of sloughed colonic mast cells in the sample, wherein the computerized imaging approach comprises identifying areas of the stained cell sample that include stain-positive cells, and isolating individual regions of interest in the identified areas according to a Hue, Saturation, Intensity (HSI) color model, and the computerized imaging approach comprises a definition of boundary conditions for a morphometric descriptor, wherein the isolated individual regions of interest comprise a Hue value between 214 and 255, a Saturation value between 15 and 208, and an Intensity value between 61 and 150;
   wherein the presence of the sloughed colonic mast cells in the cell sample indicates the presence of colorectal cancer or precancerous polyps in the colon of the subject.

* * * * *